(12) United States Patent
Conteas

(10) Patent No.: US 11,350,817 B2
(45) Date of Patent: Jun. 7, 2022

(54) WATER CYCLING COLONOSCOPY SYSTEM AND METHOD FOR USING SAME

(71) Applicant: Chris N. Conteas, Porter Ranch, CA (US)

(72) Inventor: Chris N. Conteas, Porter Ranch, CA (US)

(*) Notice: Subject to any disclaimer, the term of this patent is extended or adjusted under 35 U.S.C. 154(b) by 0 days.

(21) Appl. No.: 17/383,935

(22) Filed: Jul. 23, 2021

(65) Prior Publication Data

US 2022/0031151 A1 Feb. 3, 2022

Related U.S. Application Data

(60) Provisional application No. 63/057,625, filed on Jul. 28, 2020.

(51) Int. Cl.
| | |
|---|---|
| *A61B 1/015* | (2006.01) |
| *A61B 1/31* | (2006.01) |
| *A61B 1/00* | (2006.01) |
| *A61B 1/018* | (2006.01) |

(52) U.S. Cl.
CPC .......... *A61B 1/015* (2013.01); *A61B 1/00135* (2013.01); *A61B 1/00137* (2013.01); *A61B 1/018* (2013.01); *A61B 1/31* (2013.01)

(58) Field of Classification Search
CPC ............ A61B 1/00094; A61B 1/00135; A61B 1/00154; A61B 1/015; A61B 1/12; A61B 1/126; A61B 1/31; A61B 17/3415; A61B 17/3423; A61B 2017/3419; A61B 2017/3452; A61B 2017/3486; A61B 2017/3492; A61M 3/0295; A61M 2039/0273; A61M 2039/0276; A61M 2039/0279; A61M 2039/0288; A61M 2039/0297; A61M 2039/062; A61M 2039/0626; A61F 5/441

See application file for complete search history.

(56) References Cited

U.S. PATENT DOCUMENTS

| | | | | | |
|---|---|---|---|---|---|
| 5,620,408 | A | * | 4/1997 | Vennes | A61B 1/00154 128/200.26 |
| 5,842,971 | A | * | 12/1998 | Yoon | A61B 17/3439 600/101 |
| 5,941,815 | A | * | 8/1999 | Chang | A61B 1/31 600/114 |
| 6,234,958 | B1 | * | 5/2001 | Snoke | A61B 1/00082 600/106 |

(Continued)

FOREIGN PATENT DOCUMENTS

EP 2868335 A1 * 5/2015 ............. A61M 1/86

*Primary Examiner* — Michael J Carey
*Assistant Examiner* — Stephen Floyd London
(74) *Attorney, Agent, or Firm* — Fulwider Patton LLP

(57) ABSTRACT

The present invention is a system and method for water cycling colonoscopy that includes a colonoscope with a water ejection system and a camera, and a rectal overtube that receives the colonoscope therein. The overtube is placed in the anus and has a vacuum port outside the anus that attaches to a vacuum source. The overtube vacuum port vacuums water emitted by the colonoscope while the colonoscope is moving through the colonic lumen to control the amount of fluid in the colonic lumen. The overtube may be fitted with structures to improve the fit and attachment to the anus, including an inflatable cuff and a flexible skirt.

15 Claims, 9 Drawing Sheets

(56) References Cited

U.S. PATENT DOCUMENTS

| | | | |
|---|---|---|---|
| 6,695,772 B1* | 2/2004 | Bon | A61B 17/3421 600/114 |
| 6,808,492 B2* | 10/2004 | Snyder | A61B 17/3421 600/114 |
| 2005/0124856 A1* | 6/2005 | Fujikura | A61M 25/0662 600/115 |
| 2005/0209607 A1* | 9/2005 | Lipchitz | A61B 17/3421 606/108 |
| 2009/0062607 A1* | 3/2009 | Kucklick | A61M 25/0662 600/114 |
| 2010/0191065 A1* | 7/2010 | Fowler | A61B 17/06061 600/210 |
| 2010/0256447 A1* | 10/2010 | Dubi | A61B 1/31 600/115 |
| 2011/0144440 A1* | 6/2011 | Cropper | A61B 17/3421 600/203 |
| 2014/0318582 A1* | 10/2014 | Mowlai-Ashtiani | A61B 90/70 134/22.11 |
| 2015/0073223 A1* | 3/2015 | Pravongviengkham | B29D 23/00 600/207 |
| 2015/0141943 A1* | 5/2015 | Koch | A61M 1/0001 604/320 |
| 2016/0067148 A1* | 3/2016 | Nordquist | A61M 39/10 604/28 |
| 2017/0360281 A1* | 12/2017 | Ponsky | A61B 1/018 |
| 2018/0142787 A1* | 5/2018 | Herzog | F16J 15/022 |
| 2018/0206866 A1* | 7/2018 | Wan | A61B 17/2202 |
| 2021/0023351 A1* | 1/2021 | Lovasz | A61M 31/00 |
| 2021/0251654 A1* | 8/2021 | Pegman | A61M 13/003 |

\* cited by examiner

WATER CYCLING COLONOSCOPY SYSTEM AND METHOD FOR USING SAME

CROSS-REFERENCES TO RELATED APPLICATIONS

This application claims priority from U.S. Provisional Patent Application No. 63/057,625, filed Jul. 28, 2020, the content of which is incorporated by reference herein in its entirety.

BACKGROUND OF THE INVENTION

Colonoscopy, both diagnostic and therapeutic, has become an important part of medical care in the United States. Over 19 million colonoscopies were performed in 2017; the numbers are increasing every year. Complicating this amazing accomplishment is a 4-25% rate of incomplete colonoscopies, increasing with age up to a rate of 22-33%. The reasons for their incompletion are multiple. Redundant or tortuous colon (particularly the sigmoid colon), marked diverticular disease, obstructing masses and strictures, angulation or fixation of colonic loops, adhesions due to previous surgery, spasm of the colon, poor preparation, female sex, older age, lower body mass index and pain are but a few reasons for this dilemma. Improvement in colonoscopic technique is necessary to surmount these issues.

Traditional colonoscopy begins with proper positioning of the patient on the endoscopy table in the left lateral decubitus position with the patient's thighs flexed to a ninety-degree angle to their trunk. Vital signs are taken and anesthesia or conscious sedation is given. Prior to the anesthesia, a rectal exam is performed to check for masses, strictures, blood, solid or liquid stool in the rectal vault and to help relax the rectal musculature before the procedure. The colonoscope is tested for proper function of all component parts, air and water systems, vacuum system, picture quality of the camera, full deflection of the controls for the insertion tube and patency of the vacuum/biopsy channel.

The insertion tube, the long flexible component of the colonoscope, is inserted into the anus. It is advanced by direct forward pressure combined with the angulation of the tube by movement of the up and down and right and left controls on the control handle of the colonoscope which deflect the distal end of the colonoscope in the desired direction and by proper torque motions from the wrist of the endoscopist. Air insufflation is used judiciously to open the lumen of the colon for inspection. A water jet produced by an attached water pump acting through the colonoscope cleanses the mucosal surface of the colon. Air and liquid is removed through the vacuum instrument channel. Particular care in insufflation and suction is necessary to prevent overdistention of the abdomen and colon, overangulation of the colon, clogging of the vacuum instrument channel and patient discomfort. All areas of the colon are viewed in detail especially in areas behind haustral folds.

The vacuum instrument channel is important for performance of colonoscopic interventions. Biopsy forceps are used for histologic study of the mucosa (inflammatory bowel disease) or lesions (masses, polyps, and cancer). Braided wire metal snares for cold and hot snare polypectomy are used to cut and remove colonic lesions, principally polyps. An electric "needle knife" and injection needle system is used to uplift and remove large sessile polyps (EMR-Endomucosal Resection) from the mucosa of the colonic wall. Clips for hemostasis and approximation of mucosal tears and perforation can be deployed through use of the colonoscope. Electrocautery can be performed via colonoscopy with a BICAPP unit. Removal of tissue or small lesions may be performed via the channel, larger ones using a "basket-like" apparatus inserted via instrument channel, necessitating removal of the colonoscope to retrieve the polyp.

Colonoscopic passage during the procedure extends from the anal canal, rectum, descending colon, transverse colon, ascending colon and ending in the cecum. Colonoscopic intubation of the terminal ileum, the most distal area of the small intestine may be necessary in specific cases. The standard form of colonoscopy using air insufflation may cause the distention of the colon and abdomen increasing angulation of the colon and necessitating manual compression of the abdomen in multiple spots and the rolling of the patient from the initial left lateral decubitus position to the supine position then to the right lateral decubitus position and, on occasion, the prone position to pass areas of extreme angulation, tortuosity, structuring or partial obstruction.

When the insertion phase has been completed, the insertion tube is carefully removed performing the same observation techniques employed on entrance. It is recommended that the removal rate of the insertion tube should be between 6-10 minutes to optimize surveillance. Before removal of the insertion tube, the end of the colonoscope is retroflexed (proximal 15 cm of insertion tube) back upon itself approximately 180 degrees to view the lower rectum for pathology. Insertion tube is then straightened and removed.

The design and construction of the contemporary colonoscope, no matter the manufacturer, is all basically the same. It's raison d'etre is the visualization of the colonic and terminal ileal interior (lumen and walls of the colon and distal small intestine) for the purpose of diagnoses and treatment. This is made possible by high resolution digital optics, and efficient manual insertion system for the optics, ergonomic controls for the insertion system, water, air, vacuum systems and photographic controls and sophisticated software and hardware to support these functions.

The insertion tube is probably the most characteristic and easily identified feature of the colonoscope. The colonoscope insertion tube advances the digital camera on its distal end through the colon and distal small intestine and is the critical conduit aiding in its role for observation and intervention. Its length is variable depending upon whether it is for pediatric or adult colonoscopy, generally between 1330-1700 mm. Insertion tube diameters are between 9.5-15 mm. Biopsy instrument/vacuum channel diameters are between 2.8-4.2 mm and number between 1-2 per colonoscope. The section of the insertion tube closest to the distal end of the insertion tube, the Bending Section, possess the ability to angulate between 0-160 degrees in R/L direction (R=right, L=left) and 0-180 degrees in the U/D direction (U=up, D=down) via use of angulation of knobs and locks. This is important for helping the colonoscope negotiate passage through the terminal ileum and colon, better visualization of the ileal and colonic lumen and walls and performance of colonoscopic interventions. The insertion tube is the only part of the colonoscope to enter the patient.

The insertion tube is constructed of several components. An objective lens and solid-state sensor CCD unit-charge coupled device visualizes the colon and distal ileum, converting light images to electrical signals. A light guide lens with illumination using quartz fibers provides the lights to see in the darkness of the colonic and small intestinal lumens. An air/water nozzle cleans the objective lens free of materials obstructing its view. It is also used to insufflate the colon and distal ileum with air. The water jet cleanses the luminal wall free of adherent material, breaks up fecal material for removal and instills water in the colon-especially for WAC (WE and WI). A biopsy/vacuum channel serves a dual purpose as a conduit for the passage of instruments used in biopsy, endomucosal resection (removal of large, flat polyps/polypoid lesions), polypectomy, hemostasis, repair of mucosal and wall damage and a vacuum system to remove air, water, sediment, sludge, small polyps and blood. It is only recommended for use with air or clean to minimally soiled liquids.

Three valves are located on the control section of the colonoscope. The most distal is the biopsy valve covering the biopsy/vacuum channel. This covers the insertion port for the channel through which instrumentation for the previously described colonoscopic interventions are passed. This keeps the channel air and water-tight. A small slit in the valve (elastomer) allows instruments to pass through the valve into the channel but will form an air and water-tight seal with instruments in place or removed. An air/water valve is in a proximal position to the biopsy valve, usually above the angulation controls. Complete depression of the valve activates water release for the cleansing of the objective lens of obstructed material. Covering the vent hole on top of the valve allows air to insufflate the bowel lumen. The suction valve is immediately proximal to the air/water valve. Depression of the valve allows the opening of the biopsy channel to the vacuum system attached to the colonoscope. The significance of the vacuum system to colonoscopy has been previously mentioned. Proximal to the valves are remote switches used in photographic imaging.

A universal cord is an umbilical structure supporting all the previously mentioned duties of the colonoscope. Air, water, vacuum lines, light fibers, and CCD wiring for the colonoscope are present in this structure. An integral pumping system provides the pressure for the movement of both air and water. Water comes from its own reservoir and the air from ambient air in the room. The vacuum source used is from either a built-in wall type or portable unit. The quartz fibers of the illumination system are directed from an integral light source which is part of the supporting hardware of the colonoscope. Wire connection from the CCD is directed through the universal cord to a connector which is then attached to the video processor by its own umbilical cord.

This overview of the construction of the colonoscope presented but a cursory glance at the sophistication of the device. It, more importantly, introduces a major drawback of the colonoscopic process, present since its inception. The drawback in question is air. The basic design of the colonoscope, first used in 1969, has remained fundamentally the same to the present time. Even with tremendous advances to many of the various facets related to its systems, function and utility, it is still hampered by one of the key principles upon which it was developed. It is the use of air in the endoscopic process. Air is important for the insufflation of the colon. It serves to "open up" the colonic lumen (internal space within the colon's walls) for observation and intervention. Time honored and effective, certain shortcomings related to the nature of air have proven problematic to the performance of colonoscopy.

Air is light, lighter than water, blood, stool or tissue. It tends to rise and flow through the colon even with local insufflation of the colon with air to look at a specific area, the air tends to spread throughout the colon. This expands not only the site of insufflation; it also expands other areas of the colon while producing elongation of the colon. This is counterproductive to good colonoscopy. In the proper positioning for colonoscopy of the patient, on their left side with hips flexed, insufflation of the colon may cause it to rise in the abdomen, especially the left side of the colon. This can produce increased distention, tortuosity, angulation, and rigidity especially in the sigmoid colon, splenic and hepatic flexures.

These areas are noted for being prone to tortuosity caused by the frequently excessive length of these colonic segments. Insufflation can exaggerate this effect by the entrapment of air. This makes it more difficult for the colonoscope to pass through the colon, often making colonoscopy take longer to complete. Frequently, this produces more pain and discomfort for the patient. Pressure against the wall of the colon is problematic, especially in patients with hypersensitivity to distention noted in 30-40% of patients with irritable bowel syndrome, a condition seen in upwards of 15-20% of the US population. Tension against the mesentery of the colon, the organ which attaches the colon to the posterior abdominal wall, may produce pain as well by colonic wall displacement during the passage of the colonoscope pressing against the colon wall. "Looping" of the colonoscope is a noted side effect produced by air, inducing or exacerbating the previously described angulation, rigidity, tortuosity, elongation and dilation. These effects increase the difficulty and time duration of colonoscope passage during the procedure, often inducing spasm of the colon obstructing proper view of the lumen, necessitating increased force, increased pressure and greater pain experienced by the patient, necessitating increased anesthesia. Longer recovery time is often needed, more attention by medical personnel during and after the procedure, greater difficulty getting the patient home and longer down time once they are at home.

To potentially remedy the problems mentioned, a new technique has been developed. The technique is Water Assisted Colonoscopy (WAC) as oppose to the standard Air Insufflation (AI) Colonoscopy Technique. Water Assisted Colonoscopy (WAC) is presently classified according to two methodologies. The first is Water Immersion (WI) Colonoscopy, instilling water on insertion of the colonoscope followed by removal of the water at the time of removal of the colonoscope. The second is Water Exchange (WE) Colonoscopy where water is both infused and removed at the time of colonoscope insertion. Presently, WE appears to be the preferred technique over WI.

WE demonstrates superiority to AI in adenoma detection rate (ADR, 29.4% v. 22.9%) and polyp detection rate (PDR, 50.2% v. 39.3%). A greater proportion of painless, unsedated colonoscopies is noted with WE compared to AI. Overall, patients need less sedation, especially on demand and need less bodily manipulation during the procedure. Maximum pain scores are less in patients who had WE over AI. There also is an overall increase in patient satisfaction of WE relative to AI. This may be due to reduced angulation of the colon produced by WE, facilitating colonoscope passage with less looping of the colonoscope, especially in the left colon.

Conversely, AI demonstrates certain disadvantages to WE. The lower ADR/PDR may contribute to the documented missed ADR of as high as 22% in the literature of which 0.3% may develop interval cancers. AI colonoscopy produces greater bowel and abdominal distention with increased need for patient manipulation during colonoscopy. AI demonstrates a greater propensity to angulate the colon, increasing the difficulty in colonoscope passage, increasing the risk of procedural complications and looping of the colonoscope. This is associated with a noticeable increase in pain during AI versus WE. This pain necessitates sedation, often to high levels, necessitating closer patient monitoring during and after colonoscopy, increasing risk of mortality, prolonged patient recovery, slower patient turnover and need for more expensive and sophisticated sedation techniques such as Propofol. All these things add increased time, expense, and risk to performing colonoscopy.

Cecal intubation success rate differences are somewhat harder to differentiate from the literature between WE and AI. In experienced hands in the proper setting successful intubation rates range as high as 96-100% for AI. Closer scrutiny demonstrates areas where WE is superior to AI. These are seen in such cases as patients with abdominal and colonic surgeries, strictures and partial obstruction of the colon, mesocolon descendens, sigmoid malrotation, colonic redundancy, history of incomplete colonoscopies, as well as factors previously mentioned. Efficacy is demonstrated in minimally and unsedated colonoscopies. This will improve the worldwide unsedated cecal intubation average of 67-83% with less pain and greater patient satisfaction. WE opens the colonic lumen and weighs down the left colon, straightens the sigmoid colon and removes other areas of angulation. This facilitates passage of the colonoscope, reducing insertion pain and discomfort for the patient.

WE infuses clean water and removes this and preparatory solutions along with residual feces, sludge, sediment and retained air all while inserting the colonoscope into the colon. This improves the cleanliness of the colon with better visualization both on insertion and removal of the colonoscope compared to AI and WI, increasing chances of visualizing pathology (polyps, cancer etc.) The lesser distention of the colon using WE as opposed to AI, in addition to producing less pain and discomfort produces less distortion of the colonic topography allowing small or flat polyps to be more easily visualized. Water produces a magnification effect for better visualization of small or indistinct lesions. There is also some question that the longer intubation time with WE as compared to WI and AI may allow for better surveillance of the colon for lesions, especially on insertion. This may also be due to better cleansing, inherent with WE versus WI and AI.

WE demonstrates certain important improvements in the performance of colonoscopy. Unfortunately, there are some shortcomings which need to be addressed. It is more prone to interference by suboptimal bowel preparation. Infusing water stirs up stool sediment. It is more difficult to visualize the lumen of the colon in cloudy water. Multiple instillations and removal of water through the colonoscope may be necessary to view the lumen, also adding time to the procedure. Sediment often clogs the colonoscope. If unsuccessful at cleansing the colon and the colonoscope vacuum channel becomes clogged with stool, the procedure will need to be rescheduled. This adds inconvenience, time and expense to both patient and GI department. The prolonged insertion time of WE (16.4 min.) as compared to AI (6.3 min.) and WI (5.7 min.) will discourage its widespread application in current busy clinical practices. The additional time needed for infusion and suction and infusion and suction again and again as necessary through the colonoscope can add significantly to the time necessary for cecal intubation. This would not appeal to most endoscopists thus hindering its widespread use. It is also a messy procedure with frequent spillage of feculent effluent during and after the procedure. This produces cleaning issues related to the patient, endoscopy table and floor. This would increase endoscopy suite turnaround time and poor patient, nurse and physician acceptance. Finally, it is a more difficult procedure to master than AI or WI, further complicating universal acceptance.

Mechanistically, WE is only a WAC during the insertion of the colonoscope. Water is instilled and removed during the insertion of the colonoscope with water being removed, especially from the right colon (cecum), prior to insufflation of the colon with air during extraction. It is air insufflation on extraction replacing the water exchange during insertion.

Colonoscopy is characterized by the two above mentioned phases, insertion, and extraction of the colonoscope. Of the two, the extraction phase maybe the most important. It has its own colonoscopy quality performance metric requiring a withdrawal time of six minutes or more for optimized polyp surveillance. The insertion phase has no such metric. This is a seemingly paradoxical situation, using the inferior technique (AI) during the diagnostically more important phase of colonoscopy (extraction). Comparing the enhanced rates of adenoma (ADR-6.5%) and polyp (PDR-10.8%) detection with WE over AI to missed ADR's as high as 22% in tandem AI colonoscopies there is some reason to question that even the preferred methodology (WE) is the optimized technique for WAC.

Quality of preparation is probably the most consistently problematic issue in colonoscopy, be it AI or WE. Suboptimal rates of preparation are associated with polyp miss rates as high as 42% and advanced adenomas of 27%. The fact that WAC is inefficiently performed only during the first half (insertion) of the colonoscopy using WE, the less clinically important of the two. This suggests there is significant room for WAC improvement over WE in order to apply the concepts as related to the advantages of WE to the whole colonoscopy, insertion and extraction, with better surveillance and cleansing during both phases.

The endoscopic reduction of sigmoid volvulus finds WE to be useful. Endoscopic detorsion, minimizing air introduction along with good visualization with minimal water inflation may reduce intraluminal pressure, pain and risk of colonic perforation. More recent studies have shown success in 21 patients with a total of 71 endoscopic detorsion procedures using WI without sedation. All procedures were successful. No procedural complications were incurred, and no surgery was necessary in any of the cases.

AI causes colonic spasms and contractions. Colonic spasm around larger lesions in an air-filled colon interferes with the removal of the lesion. This is especially difficult in the sigmoid colon which may not retain air and maintain luminal distention. Water distention straightens out the sigmoid colon, air tends to cause angulation of the sigmoid colon in the left lateral decubitus position, the preferred position for colonoscopy. WI has been used for endomucosal resection (EMR) of large colonic polyps by filling the sigmoid colon with clear, clean water distending the lumen enough for easy underwater polyp visualization. Underwater endomucosal resection (UEMR) is good for removal of lesions of varying sizes, forms, and locations. It is useful in difficult polypectomy cases and potential salvage interventions when AI was unsuccessful. It eliminated the need for submucosal injection and was useful for salvage treatment of recurrent adenomas with fibrosis after piecemeal EMR. Compared to EMR, UEMR increases the proportion of complete resections of medium to large-sized lesions and reduces the proportion of recurrences, post treatment bleeding, transmucosal burns and perforation. Water does not affect the conductivity of the tissue during polypectomy, cold as well as hot snare polypectomy can be safely executed in a water-filled lumen. Water acts as a heat sink and prevents direct contact of the polyp tip with a nearby colonic wall; thus, UEMR can minimize risk of contralateral mucosal burns during polypectomy. The major limitation of UEMR is that is does not work well under conditions of poor bowel preparation. This is due to poor visualization of the lesion.

Water Assisted Colonoscopy (WAC), especially WE, holds much promise, for improving the performance of diagnostic and therapeutic colonoscopies. Its future success depends on the improvements in certain areas, such as improvements of its cleansing capabilities, faster intubation of the cecum, less messiness and ease in mastering the system. These improvements must be accomplished without compromising the established benefits of WE, namely, ease of use, effectiveness, etc. are critical to WAC.

SUMMARY OF THE INVENTION

The present invention relates to a system for implementing an improved Water Cycling Colonoscopy (WC) that is designed to meet and solve the previously mentioned shortcomings observed with the present WAC (WE and WI). WC is especially suited for specialized colonoscopic situations, including patients with poor preparation by history and previous incomplete or difficult colonoscopies. Other factors include age, constipation, narcotic use, antidepressants, and other constipation inducing medications, and decreased mobility to name but a few. Additionally, actual or potentially difficult colonoscopies due to complicated anatomy, previous surgeries, and adhesions, small or slight body habitus, tall or obese habitus, previous need for excessive pain medication, especially with poor effect and those patients who needed vigorous abdominal pressure or frequent position change during the procedure will be candidates as well. Patients who are to have an anesthesia-free procedure are especially likely to profit from WC.

Future areas of importance for WC include the previously described sigmoid volvulus, UEMR and treatment of lower GI bleeding. It is also believed to be very well suited for use with therapeutic colonoscopy.

WAC is a methodology gaining wider acceptance. WI and WE, while performed in a different manner, are simply different applications of the same process. They utilize only the vacuum and water infusion systems of the colonoscope, nothing more. This is either in a unidirectional fashion of water infusion on entrance with its removal by suction at the time of removal of the colonoscope (WI) or alternating water infusion and suction during the insertion of the colonoscope (WE). One technique is faster and easier (WI) and the other is slower and technically more difficult but with higher ADR/PDR and even less discomfort (WE). Both are messy and strongly negatively affected by poor preparation.

The fault is largely due to the basic system. While the water delivery system is adequate for its desired purpose, the vacuum system for removing the fluid and waste is more problematic. This is because the colonoscope has only a narrow channel to transport the matter back outside the body, and this narrow channel is easily blocked by stool, sludge, sediment, and dirty water. Moreover, the dirty water, sludge, sediment, and stool by the design of the colonoscope is unfortunately drawn into the visual field of the colonoscope during the removal process, resulting in poor visibility that, if unresolved, can lead to the procedure being terminated and rescheduled.

A system that performs a simultaneous water infusion and water/waste removal is highly desirable. This results in a more effective removal process for the mobilized and solubilize waste removed from the colon by the water infusion. Keeping the camera lens and vacuum/instrument channel of the colonoscope clear of debris is vital to ensuring a positive result, as this greatly improves luminal visibility, gives greater protection to the vacuum instrument channel during the procedure, and produces a faster colonoscopy. It is an easier and simpler process as well as a cleaner, less messy one to perform. Enhancement of the ability to more finely control distention of the colon during the procedure greatly adds to patient comfort and safety.

Water Cycling Colonoscopy possesses design innovations that solves the previously stated problems. Instead of using the vacuum system of the colonoscope with the problems previously mentioned, a second source for the removal of waste materials and gas is positioned at a proximal site, namely the anal canal. Water is still infused from the colonoscope, either intermittently or continuously, but rather than being suctioned back into the vacuum system of the colonoscope the effluent is suctioned proximally through the colon and out a rectal overtube. This system employs the strengths of WI— constant water infusion on entrance with a faster procedure and the exchange process of WE with a better ADR/PDR and greater patient comfort. This system has a better cleansing capability than that of contemporary WAC, either WI or WE, in a simple system easily adapted to any circumstance where colonoscopy is now being performed. It is easily set up, intuitive and easily mastered. The overtube ensures a cleaner as well as more controlled procedure.

The water cycling system of the present invention suctions waste away from the colonoscope camera lens and vacuum area to the distal overtube vacuum system, while constantly replacing dirty, cloudy water and waste with clean, clear water (continuously or intermittently) as necessary for a cleaner more rapidly obtained visual field. There is no need to suction waste into the channel of the colonoscope, and no necessity for alternating between water infusion and suction through the colonoscope as was required heretofore. The alternating of fluid introduction and removal significantly slows the insertion process and leads to frequent clogging of the channel, and the present invention eliminates this requirement. Water infusion and vacuum removal can be independently controlled to account for such conditions as proper distention of the colon for better visualization of smaller flat polyps, pain management, and better patient acceptance and foreshortening of the colon for a faster procedure.

The messiness of the procedure due to anal leakage of waste, water and stool during the procedure is addressed not only by the rectal overtube but by the adhesive binding of a skirt-like attachment on the overtube. This helps to keep the tube in proper position in the anal canal and provide an air and water-tight seal against leakage around the overtube. This skirt is preferably attached around the outside of the overtube and can be moved into contact with the patient to anchor the overtube in place while establishing a seal around the overtube. The patient is relieved of contact with the waste, and the exam table and floor are kept cleaner. The procedure is more sanitary, with easier patient and endoscopy suite turnover with better patient and staff acceptance. The overtube may also include a second anchoring device that expands once inside the patient's colon, either through inflation or by mechanical means, as explained more fully below.

If a more vigorous cleansing is necessary due to thicker sludge or stool fragments a covering over the insertion port for the colonoscope can be removed to create a larger opening for waste to exit in the presence of either water pressure, gravity, vacuum, or abdominal pressure. Since this waste exits through the overtube its disposal can be managed easily using a collection bag, basin, reservoir, etc. The overtube covering, which when in place forms an air-tight and water-tight connection, that can be removed and replaced as needed during the procedure. This feature permits the ability to perform procedures such as polypectomies, UEMR, treatment of lower GI bleeding and volvulus reduction during the colonoscopy.

The water cycling system of the present invention is simple and can be set up in a few minutes in basically any appropriate hospital setting. The proposed system is composed of two separate component parts. The first component is a colonoscope with a water infusion system and the second component is a rectal overtube with a vacuum system. The arrangement continues to make use of the colonoscope's water infusion system in much the same manner as water immersion WI and water exchange WE colonoscopy. This is for cleaning the colon and filling the lumen with water. There is much less reliance on the vacuum system of the colonoscope to prevent it from being clogged. Use of the colonoscope water infusion but not water extraction allows for faster cleansing and decreased colonoscopic transit time to cecum. The vacuum channel of the colonoscope is freed for use in gas removal, biopsy extraction, hemostasis, polyp removal, UEMR and related therapeutic and diagnostic interventions.

The rectal overtube is used to traverse the anal canal from the perineum to the proximal rectum and is preferably composed of an elastomer with a hydromer coating. This provides some flexibility with ease of insertion and greater and easier volume movement of waste material than through the colonoscope's vacuum channel, with less chance of clogging. The flexibility makes the overtube more comfortable, easier to use, and safer for the patient.

The rectal overtube may as an example be 10.0 cm in length and 2.5 cm in outer diameter in one preferred embodiment. Its most distal half is devoted to its stabilization and conduit function inside the anal canal. The overtube may further include an inflatable component that can be inflated into an inverted cone using air or water. To inflate the component, a tube running through the distal segment of the overtube connects at an inflation port. It is placed into the anal canal and inflated when in proper position. This form fits the proximal rectum and distal anal canal due to the flexible nature of the mechanism and the disparity of the larger diameter of the distal end of this segment to the diameter of the more proximal part of this segment of the overtube helps to secure the overtube in the anal canal. This inflatable anchor holds the overtube in place and helps it remain in an air-tight and water-tight relationship with the surrounding tissue.

In an alternate system the inflatable distal section of the overtube is replaced with a mechanically expanding mechanism. That is, instead of inflation of the distal segment of the overtube with air or water, an umbrella type mechanism or other mechanical expansion type keeps the distal end of the overtube in the closed position. When released, it can assume a default position of fully open. This is opposite of the inflatable system, which must be positively inflated to achieve the closed position. A flexible elastomer may be used to reinforce the device and allow it to stay in the open position using a snare-like apparatus around the distal end of the overtube to keep it closed around the insertion tube. Releasing the snare allows the distal opening to enlarge and form a cone shape in similar fashion to the inflation system. This is controlled by the forward and backward movement of a button-like attachment that slides along a groove. Strategically placed openings in the groove allows the snare to be arrested in preselected positions between fully open and fully closed as necessary for proper seating of the overtube, examination of areas of the rectum possibly covered by the distal overtube and for overtube removal.

In an alternative embodiment, the expandable distal end of the overtube is eliminated in lieu of a rigid section. The fit of the tube acts as a seal. This alternate design uses only the more proximal perineal attachment with an adhesive surface to anchor and seal the tube in place. Unlike some embodiments, this version does not use the colonoscope as an introducer but has one specifically constructed to be used independently from the insertion tube of the colonoscope. This is similar in design to an anoscope, where the introducer is fitted inside the overtube with the distal end shaped into an ogive for easy and safe insertion into the anus. Once inserted into proper position the introducer is removed, the colonoscope port covered with a flexible membrane, and the colonoscope is inserted therein. This produces a very simple, yet functional system to achieve the goals of water cycling colonoscopy.

The structure of the most proximal portion of the overtube allows for the simultaneous presence of the colonoscope while vacuuming gas, water and waste effluent through the overtube. Located on the proximal end is a port for attachment to a vacuum line. Replaceable and interchangeable attachments for the vacuum line to the overtube are available to ensure a proper connection. The vacuum system works equally with either a portable or a wall vacuum system.

The entrance to the overtube establishes a port for the insertion of the colonoscope. This port preferably includes a covering with a central hole for receiving the colonoscope, and may be constructed of a thin flexible membrane. The material preferably has a low coefficient of friction to permit smooth movement, insertion and removal of the colonoscope. The central opening is large enough for the colonoscope to pass easily while maintaining a good air and water-tight seal about the colonoscope. This covering is removable to allow for polyp extraction, foreign body removal, problematic waste disposal etc. without the need to remove the overtube. A cap for the port is employed to make the system air and water-tight in the absence of the colonoscope.

The preferential water delivery apparatus for the colonoscope is a mechanical pump with a foot control. The preferential vacuum apparatus for the overtube is either a wall vacuum unit or portable vacuum unit, although manually operated balloon pumps can also be used. In the case of machine induced vacuums, the unit may be controlled preferentially through a finger operated valve attachable to the control handle of the colonoscope. A trumpet type valve is preferred since varying the degree of opening varies the suction available. A "Y" connector may be employed in order to use the same vacuum source as the colonoscope for the sake of convenience and also if portable or built in vacuum units are in short supply. In yet another alternate embodiment, a manual siphoning system can be used to remove the fluid in the colon and drain into a collection container.

These and other benefits of the present invention are best understood in view of the detailed description of the invention below along with the accompanying drawings listed here.

DETAILED DESCRIPTION OF THE PREFERRED EMBODIMENTS

The present invention solves a critical problem found with standard WE and WI colonoscopy, namely the sole dependence on the water infusion and water, waste, and air suction capabilities of the colonoscope to perform effluent exchange. Water Cycling Colonoscopy moves the vacuum system for colonic waste, air, water, sediment, and sludge from the colonoscope to the anal canal using a short overtube system for both a new vacuum system and colonoscope insertion port. The insertion port at the entrance to the overtube can also serve as a site for removal of polyps, stool, blood, foreign material and other GI related materials. This system uses the close dimensions of its outer diameter to the anal canal and an air and water-tight seal from its attachment to the perineum to address and minimize leakage. This in turn makes the colon, with the exception of the ileocecal valve, substantially a closed system. It further presents an opportunity for greater and more sensitive monitoring and adjusting of the volume and dimensions (diameter and length) of the colon.

Figure 1:
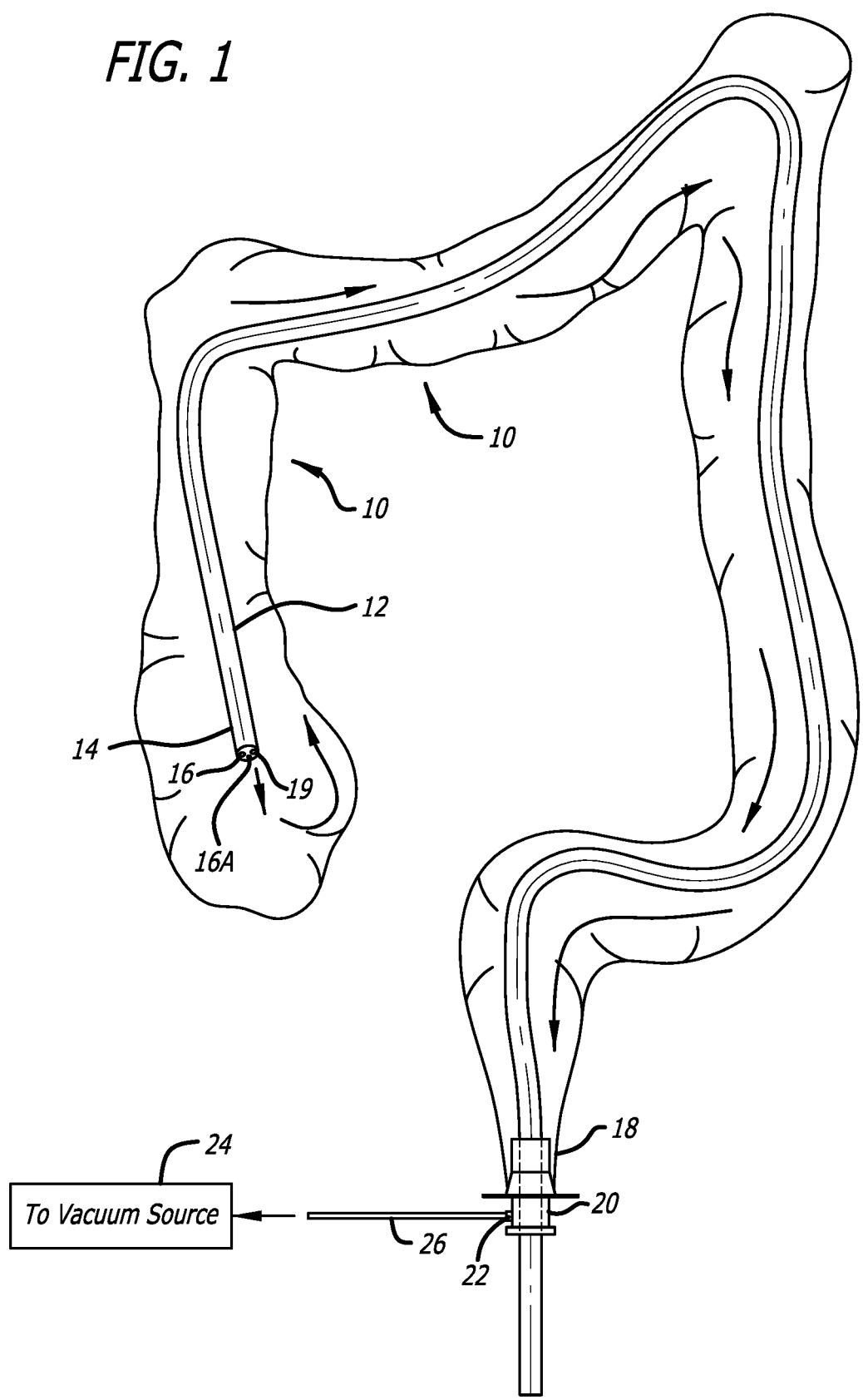
FIG. 1 is a schematic diagram of the colon and colonoscope configured for water exchange colonoscopy using the present invention.

As seen in FIG. 1, an overly simplified patient colon system 10 is shown with a colonoscope 12 inserted and extended to a distal position in the right colon. The colonoscope 12 is equipped with a water port 16 at a distal end 14 for introducing clean, fresh water at the distal position shown in FIG. 1. The port for the biopsy/vacuum channel on the end of the colonoscope 16A is the dedicated vacuum port for the colonoscope. The water cleans the inner walls of the colonic lumen while a camera sends images to a remote screen being viewed by the colonoscopist. The accumulating water infused from the distal end 14 of the colonoscope 12 serves to inflate the colon 10 and expand the folds and crevices of the wall to allow better observation via the camera 19. The colonoscope is equipped with a biopsy/vacuum port 16A to be used for procedures (polypectomy, biopsy, hemostasis, repair of mucosal trauma, and endomucosal resection), trapped gas removal and only sparingly, for fluid removal.

During Water Cycling Colonoscopy, clean, clear water is pumped through the colonoscopy and into the body lumen immediately upon insertion at the rectum 18. Special attention is paid to the use of higher water infusion volumes and infusion flow rates. The relationship of the more localized and controlled hydrostatic effect on colonic distention to pain is of particular importance. Simultaneous removal of residual air is performed to aid in water infusion and better control of colonic distention. A foot pedal (not shown) may adjust the water infusion through the colonoscope, while vacuum for air removal is actuated by a vacuum control on the colonoscope control handle. Water removal from residual colonic preparation, infused water (clear or soiled), sediment, sludge, and fragmented stool, is accomplished by suction through the overtube 20. This may be performed using a vacuum source 24 that imposes a negative pressure at the entrance of the vacuum port 22 on the overtube 20 via a vacuum tube 26. The vacuum source 24 may be controlled by using a manually controlled valve such as, for example, by a trumpet-type finger control attached to the control handle of the colonoscope. The vacuum source 24 may be a standard wall vacuum unit, common in the hospital and clinic procedures room setting, or a portable unit of the type commonly used in surgery, intensive care units and outpatient procedure settings. This draws the effluent materials away from the colonoscope 12 and the area of the water jet and objective lens at the distal end 14 of the colonoscope 12, through the colon and into the overtube 20, and from there into the vacuum waste collection receptacle (not shown). This system can easily be varied or alternated from totally infusion to totally suction to modulate between the two.

The system of the present invention produces a more effective cleansing and visualization of the mucosa. This is accomplished by constantly infusing clear, clean water from the distal end of the colonoscope 12 coordinated with a constant suction removal of accumulating dirty water, sediment, sludge and fecal material away from the distal end of the colonoscope insertion tube, specifically, the objective lens of camera 19, into the rectal overtube 20 and out through the vacuum system into a waste receptacle. This produces better and quicker visualization of the colonic wall (mucosa) and frees the water infusion lumen of the colonoscope 12 by not drawing the waste back into the colonoscope's biopsy/vacuum port 16A just millimeters away from the lens. This quicker, more accurate site picture is better for seeing potential lesions (polyps, cancer), mucosal pathology (colitis, vascular malformations), and defining strictures, adhesions and colonic malrotation.

Enhanced visualization of the colonic lumen and mucosa using a localized hydrostatic effect and shear force of the water jet helps the colonoscopist to more carefully distend and maintain the colon at a narrower diameter. This acts so as not to efface small, sessile polyps or lesions by "stretching out" the mucosa. The present invention also allows easier transition of the colonic insertion tube through a minimally, yet adequately, distended and elongated colon and into the cecum. This is related to the shared localized hydrostatic ability with water exchange/removal to prevent colonic dilation, lengthening, angulation, exaggeration of colonic tortuosity and ensuing colonoscopic looping. Particularly significant, this also produces much less pain and discomfort for the patient. Directing the waste away from the biopsy/vacuum port 16A prevents it and its channel in the insertion tube from becoming clogged which hampers interventional colonoscopy, air pocket removal and the necessity of cleaning the channel or replacing the colonoscope in the middle of the procedure or halting the procedure all together.

Stool retention in the channel may produce problems in cleansing the colonoscope, potentially damaging the colonoscope and causing potential infection risks. Infusion of water and vacuum removal by the system can be done not only upon insertion but during removal of the colonoscope, enhancing cleansing and potentially increasing ADR/PDR. Higher flow rates of water infusion increases the shear forces on the colon wall, which in turn allows for even better cleansing of the colon to enhance the surveillance capability of the colonoscope and water magnification effect improving visualization of small lesions on both insertion and removal of the colonoscope. Continuous flow of clear, clean water at higher infusion rates with constant removal of effluent or variations of these gives a more immediate clearer picture of the colon and mucosa. It provides a better, quicker, more accurate evaluation of the colon and its pathology and more rapid progression to the cecum. This is time saving, which alleviates the problematic prolonged insertion time caused by repetitive water instillation and suction through the vacuum port of the colonoscope.

The continuous flow system is helpful in the case of a poorly prepared colon. Most studies cite from 25-30% of colonoscopies as having inadequate preparation. This would be in the range in the US from between 4,750,000-5,700,000 colonoscopic procedures per year. Successful application of the present invention to the problem of poor preparation would be both medically and financially efficacious. The sealed nature of the system works well for aggressive cleansing yet maintaining cleanliness of the patient and endoscopy suite. The present invention also allows for high water flow into and out of the colon, increasing visual capability and reducing the number of failed or repeated procedures. The water flow rate also keeps the lens field of view clear of stool, blood, and debris, improving visual quality and maximizing the magnification effect of the water.

Figure 2:
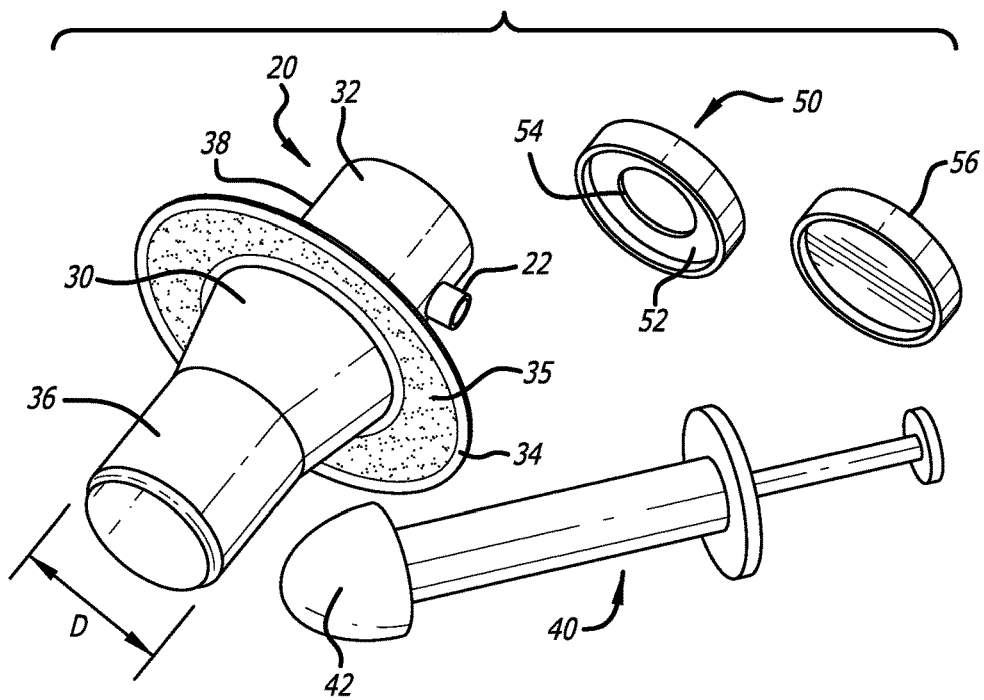
FIG. 2 is an elevated, perspective view of a first embodiment of an overtube and introducer of the present invention.
Figure 3:
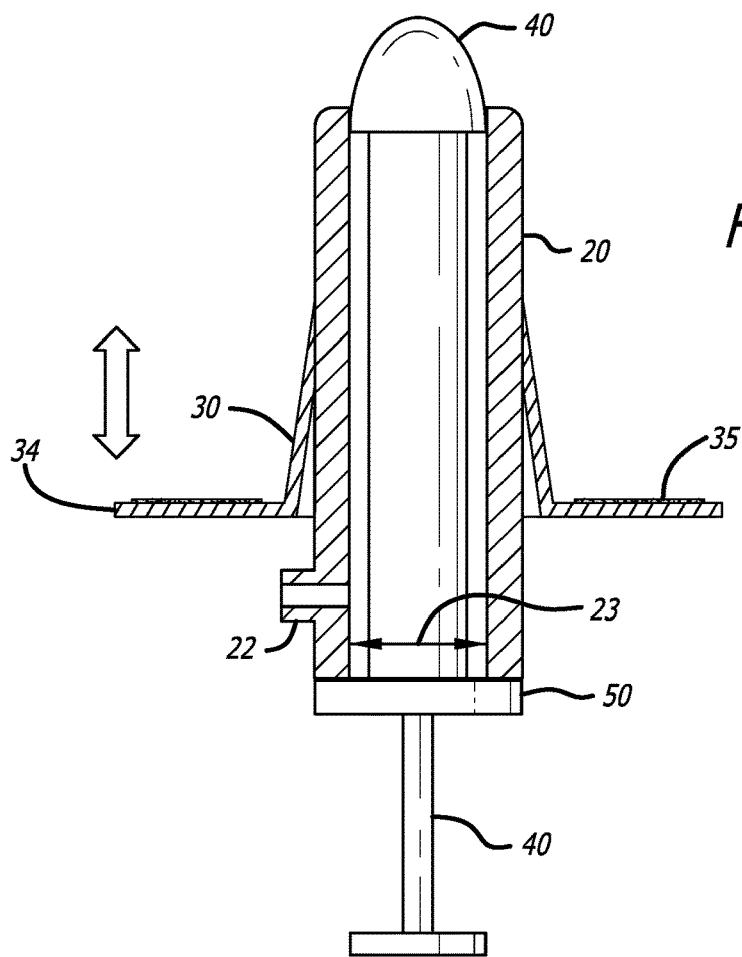
FIG. 3 is a cross sectional view of an overtube and introducer.
Figure 4:
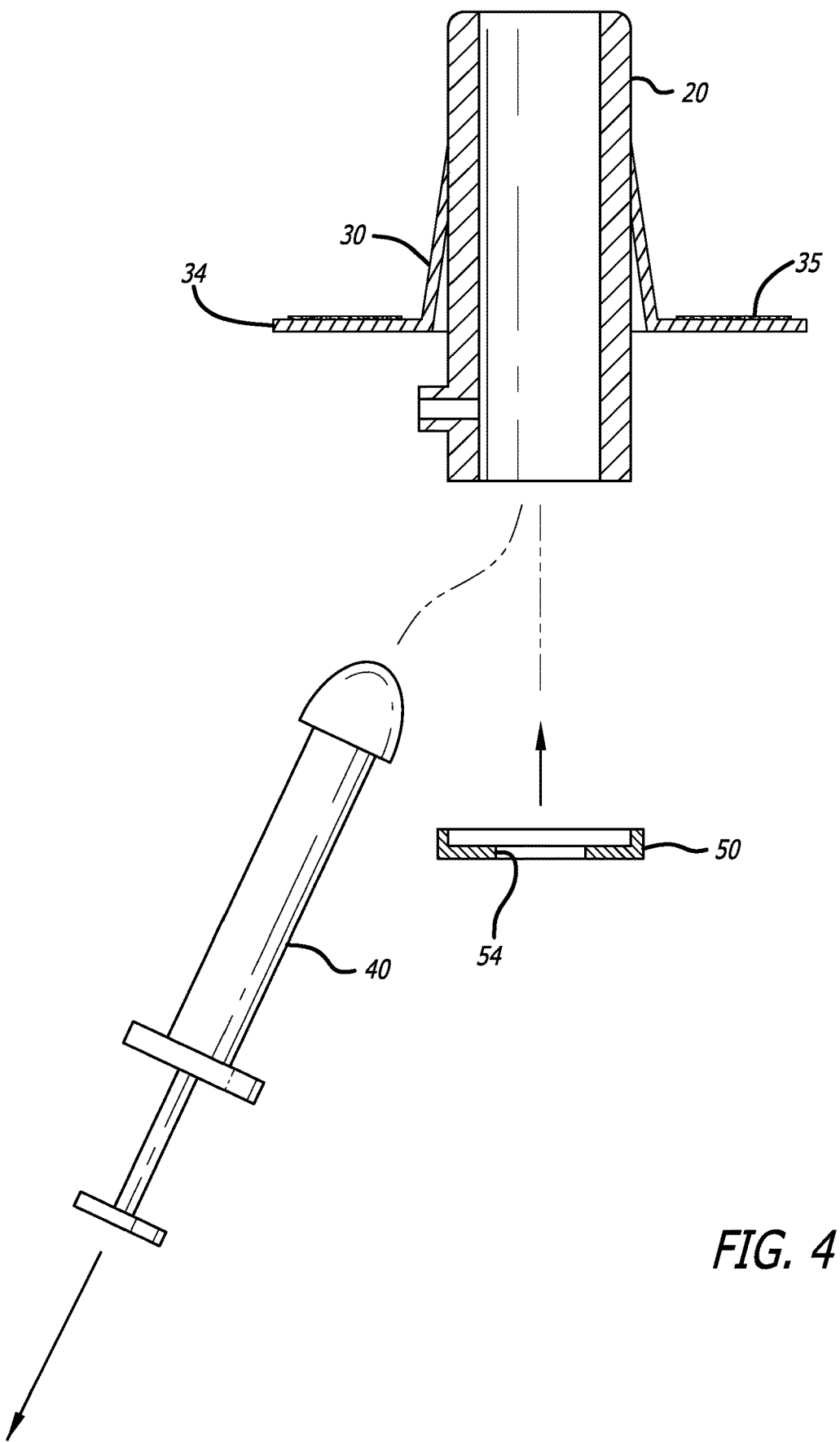
FIG. 4 is an enlarged, cross sectional view of the overtube and sealing cap.
Figure 5:
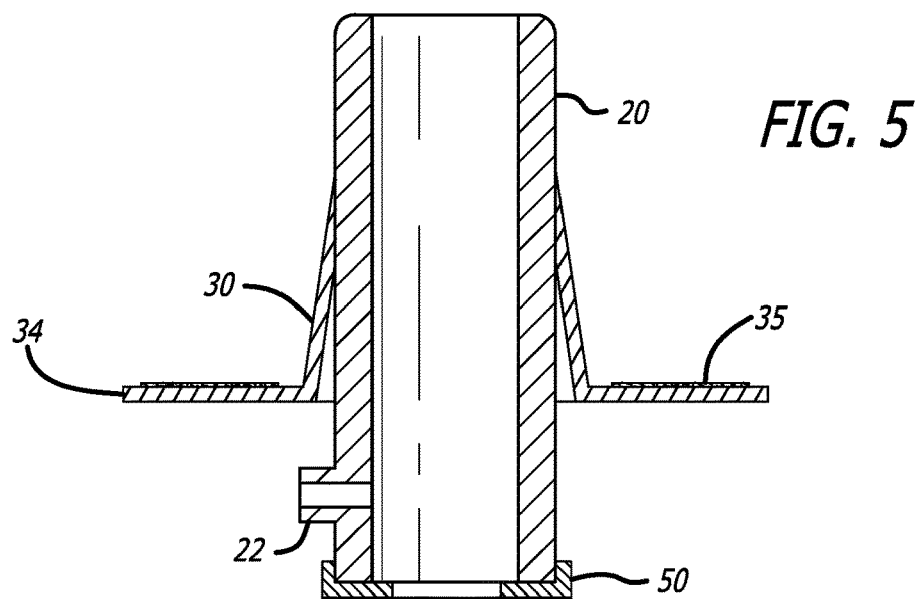
FIG. 5 is a cross sectional view of the overtube and sealing cap.

FIG. 2 illustrates one example of an overtube used in connection with the present invention. In one preferred embodiment, the overtube 20 is approximately ten centimeters in length and caries an outer diameter of approximately 2.5 centimeters. The overtube 20 includes a thin-walled flexible skirt 30 attached to the tubular element 32. The outer surface 34 of the skirt around the periphery may include an adhesive material 35 that helps the skirt attach to the patient's dermis to form a substantially air-tight and water-tight seal. The skirt also forms a stop to help position the overtube 20 in proper position within the anal canal (see FIG. 7). To facilitate insertion of the overtube 20 into the anal canal, one may employ a specifically constructed introducer 40 in a fashion similar to an anoscope. The introducer 40 is formed with a rounded distal end 42 with a diameter that fits within the inner diameter D of the overtube 20. The introducer 40 is inserted into the overtube 20, such that the distal end 42 protruded through the overtube 20 (see FIG. 3). The introducer/overtube combination is inserted into the anus to prevent the soft tissues of the anus and anal canal from being injured by the edges of the open end of the overtube 20. The introducer 40 is then withdrawn, leaving the overtube inserted in the anus so that the colonoscope can then be inserted. The system also includes a cap 56 that can be used to cover the overtube's entrance once the colonoscope is removed to seal the colonoscope and allow the vacuum to continue to remove fluid post removal of the colonoscope 12.

The fit of the overtube 20 and the incorporation of the thin walled skirt 30 and adhesive coating serves to seal the anal opening against the overtube for both air and water leakage. The skirt 30 allows the overtube to be inserted into the anal canal to seal the canal in a "plug-like" fashion. Once inserted and anchored into proper position, the proximal end of the overtube 20 is covered with a thin flexible membrane covering 50 having a central opening 54 through which the colonoscope 12 is inserted. The membrane wall 52 may be covered by a hydromer that enhances the passage of the insertion tube of the colonoscope forward and backward without losing the seal about the colonoscope.

The overtube 20 is a cylinder of approximately 2.5 centimeters in outer diameter and 10 centimeters in length, and a wall thickness of between 1-2 millimeters. It may be constructed of an elastomer to be semi rigid with slight to moderate flexibility and compressibility. The distal segment 36 is inserted into the anal canal up to the skirt 30 and remains there throughout the procedure. It serves as a conduit for the passage of the introducer 40 and the colonoscope 12 into the patient. The distal segment 36 is specially adapted to fit snuggly to establish an air-tight and water-tight seal while favoring passage of air, water, sediment, sludge, fecal material, polyps and foreign material through the tube. The proximal or external segment 38 is purposed for being the site of waste removal and colonoscope insertion.

Waste removal is accomplished in large part using a vacuum port 22. This has removable fittings (not shown) at the vacuum attachment site for connecting to standard vacuum tubing 26 of the type used in endoscopy suites and medical centers. Removability is also important to clear any blockage at or above the point of attachment should this happen while vacuuming of the waste material during the procedure. Waste is vacuumed by either a separate vacuum source 24, portable or standard wall type vacuum unit, or a "Y" type connector so that both vacuum systems of the overtube 20 and colonoscope 12 may share the same vacuum source. This proves useful where extra vacuum sources are unavailable at the time of the procedure. The vacuum system may use a trumpet type valve (not shown) to open and close the overtube 20 to the vacuum source 24. It is attached by ties and a tacky surface on the trumpet valve to the control handle of the colonoscope in an ergonomic fashion. The valve is easy to connect and disconnect from the ties to the control handle. The system is operated by one finger which is within a few centimeters of the related controls of the colonoscope.

The overtube's proximal end includes an opening or port 23 that may be approximately 2.5 cm in outer diameter with a wall thickness of 2 millimeters and has a removable membrane covering 50 made of a thin, flexible polymer membrane made of or covered with a high coefficient of friction material. The central opening for insertion of the colonoscope insertion tube is 0.8 to 1.3 centimeters in diameter, close enough for the colonoscope insertion tube to have a close air to water seal yet move easily due to the low coefficient of friction of the material. This opening allows for the performance of the usual diagnostic (biopsy, polypectomy, endomucosal resection) and therapeutic (hemostasis, colonic wall repair, volvulus reversal) colonoscopic procedures. The opening 23 also serves as an auxiliary drainage port for stool and effluent. The covering 50 is removable to allow for polyp extraction, foreign body removal, problematic waste disposal etc., without need to remove the overtube 20.

Figure 6:
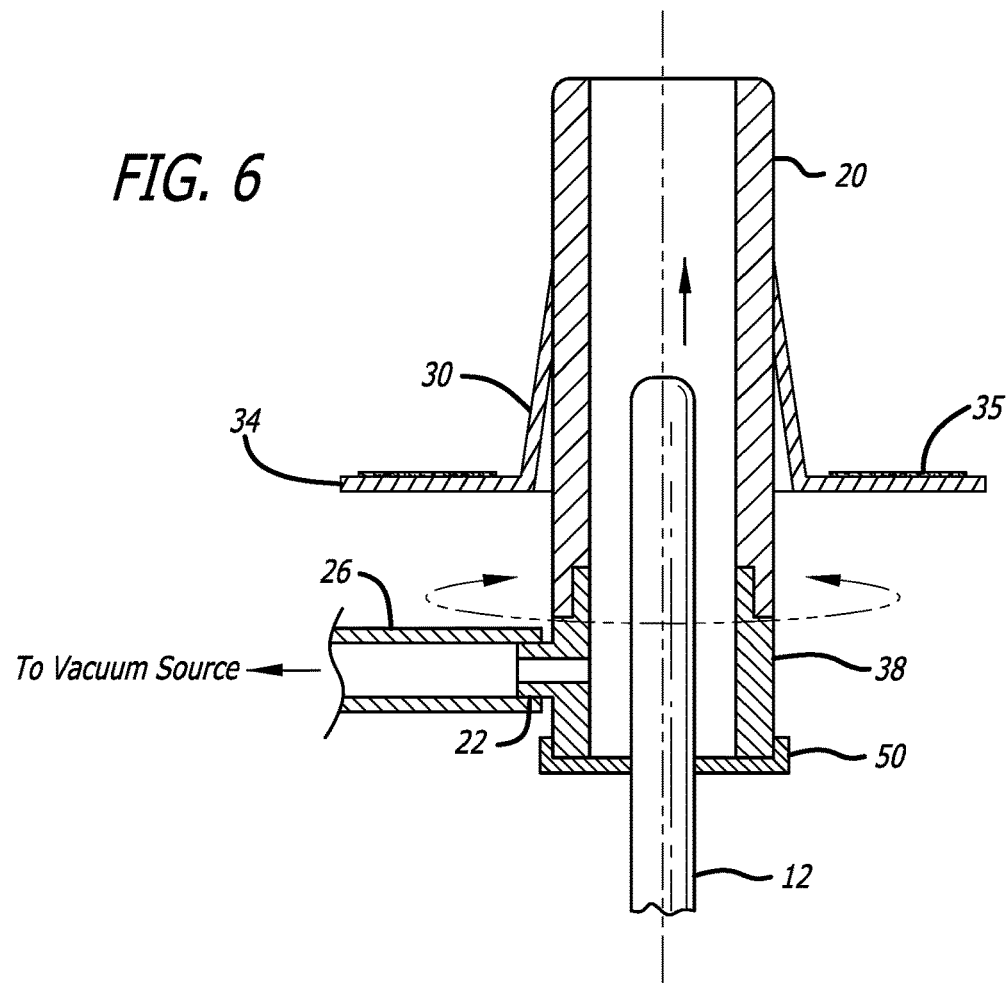
FIG. 6 is a cross sectional view of the overtube and sealing cap with a vacuum source attached to the vacuum port.

The vacuum port 22 may be positioned about 0.5 cm above the opening to the colonoscope introducer port for better drainage. It is positioned in the most proximal 2 cm of the overtube 20 on a cylindrical element 38 that can be twisted independently from the rest of the overtube through 360 degrees (see FIG. 6). This rotation keeps the waste removal port available in any suitable position for good drainage and prevents the drainage line from getting "wrapped around" the patient in the event the patient's position needs to be changed during the colonoscopy. Cap 56 occludes the overtube once the colonoscope is removed to cover opening 23.

Figure 7:
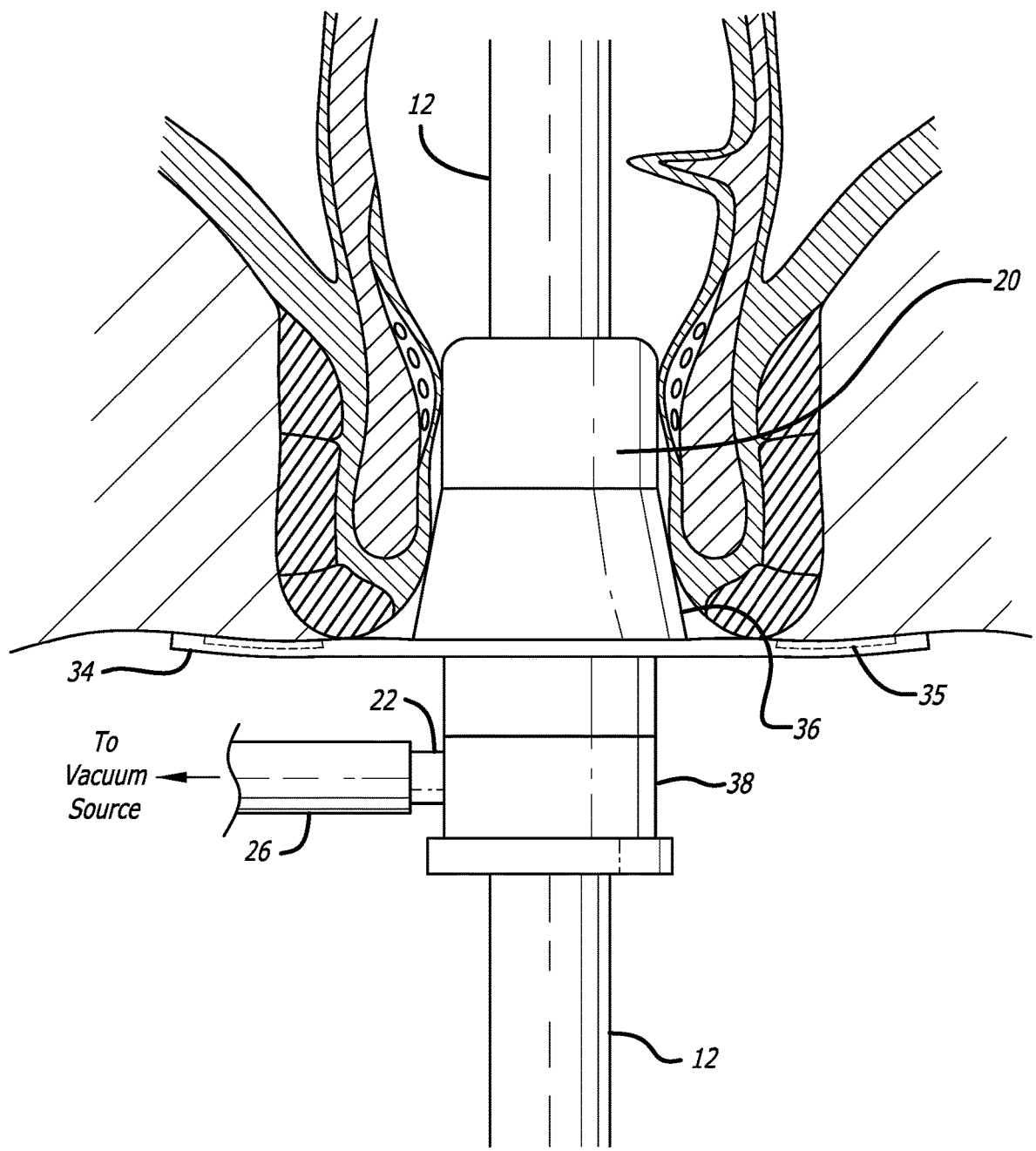
FIG. 7 is the embodiment of FIG. 6 shown in the anus with a colonoscope in the overtube.

FIG. 7 shows the overtube 20 in the patient with the colonoscope passing through the overtube. The overtube forms a fluid tight seal with the anus, and the effluent is vacuumed out the vacuum port 22 and into tube 26, where it can be collected and discarded into a bag or container. The skirt 30 attaches to the patient's buttocks and helps to seal the overtube 20 with the tissue surrounding the anus, and the adhesive coating on the surface of the skirt 30 further enhances the contact and limits leakage.

Figure 8A:
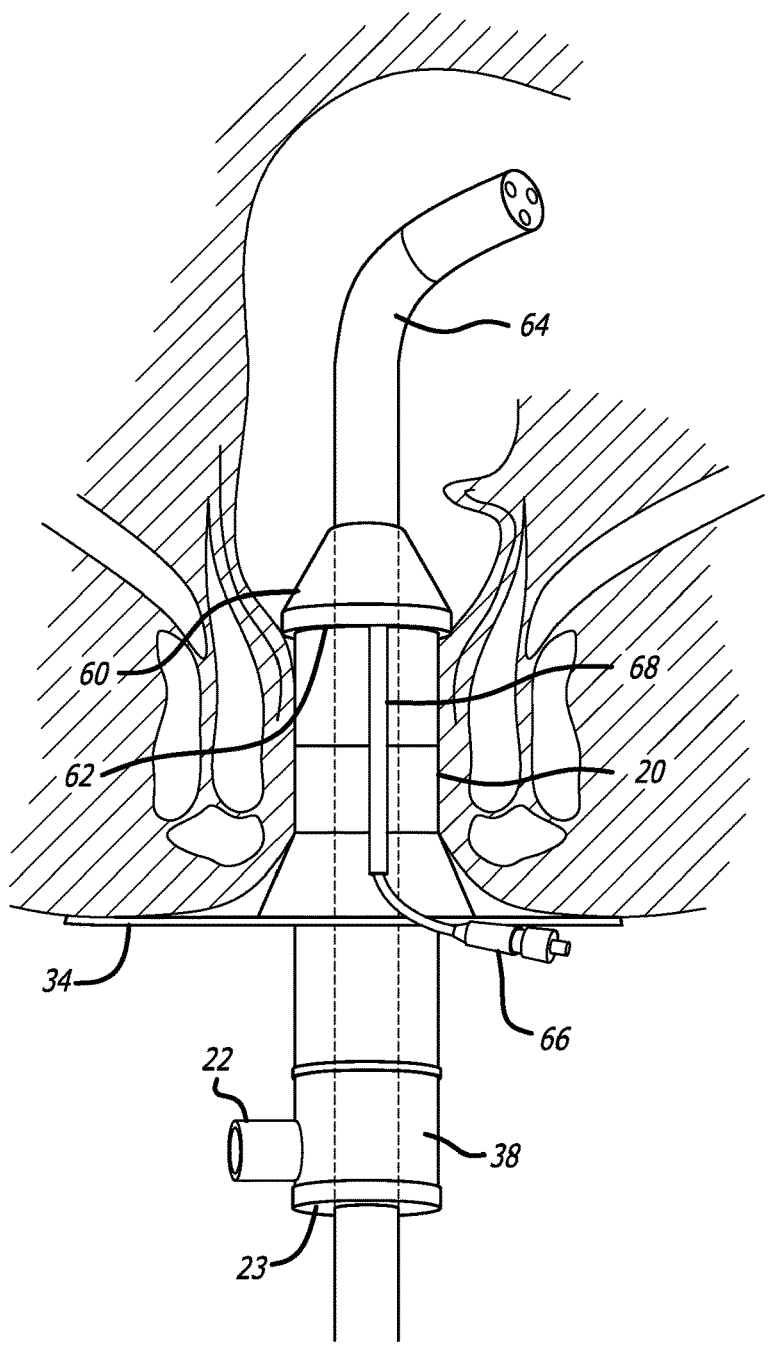
FIG. 8A illustrates an alternate embodiment of an overtube of the present invention in a closed configuration.

An alternate configuration of the overtube is shown in FIG. 8A,B and includes a low-pressure water or air inflatable cuff 60 for overtube placement and retention in the anal canal, and to help further assure prevention of air and fluid leakage around the overtube 20. The cuff 60 attaches to the end of the distal opening 62 of the overtube 20 and in the closed state surrounds both the most distal portion of the overtube and the colonoscope 12 as well. This closes the annular gap between the insertion tube 64 of the colonoscope 12 and the inner wall of the overtube. Closure of this space prevents trauma to the mucosa of the anal canal on insertion of the overtube as well as possibly obviating the need for a dedicated introducer 40. The structure now becomes a single, smooth overtube-insertion unit free of areas which would catch on the anatomy of the anal canal. Inflation of the cuff 60 through an inflation port 66 on the mid portion of the overtube via a tube 68 connecting the port 66 to the cuff 60 opens the distal opening of the overtube (reminiscent of a flower, see FIG. 8B) to permit fluid and air removal, as well as providing another anchoring point for placement and retention of the overtube 20 and establishing a seal against air and fluid leakage around the overtube.

Figure 8B:
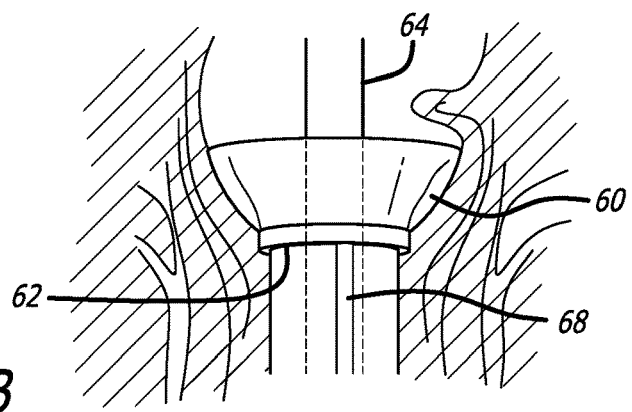
FIG. 8B illustrates an enlarged view of the alternate embodiment of the overtube of FIG. 8A in the open configuration.

When the cuff 60 is open as shown in FIG. 8B, it anchors the overtube 20 in place and cooperates with the skirt 30 to more precisely position and stabilize the overtube. Using the cuff 60 as described may obviate the need for an adhesive coating on the skirt to hold the overtube in place. The water or air inflation of the cuff 60 is atraumatic to the mucosal and other anatomic structures in the anal canal and proximal rectum. Varying the inflation of the cuff 60 can adjust the fit of the overtube 20 with anal canals of varying lengths.

Figure 9A:
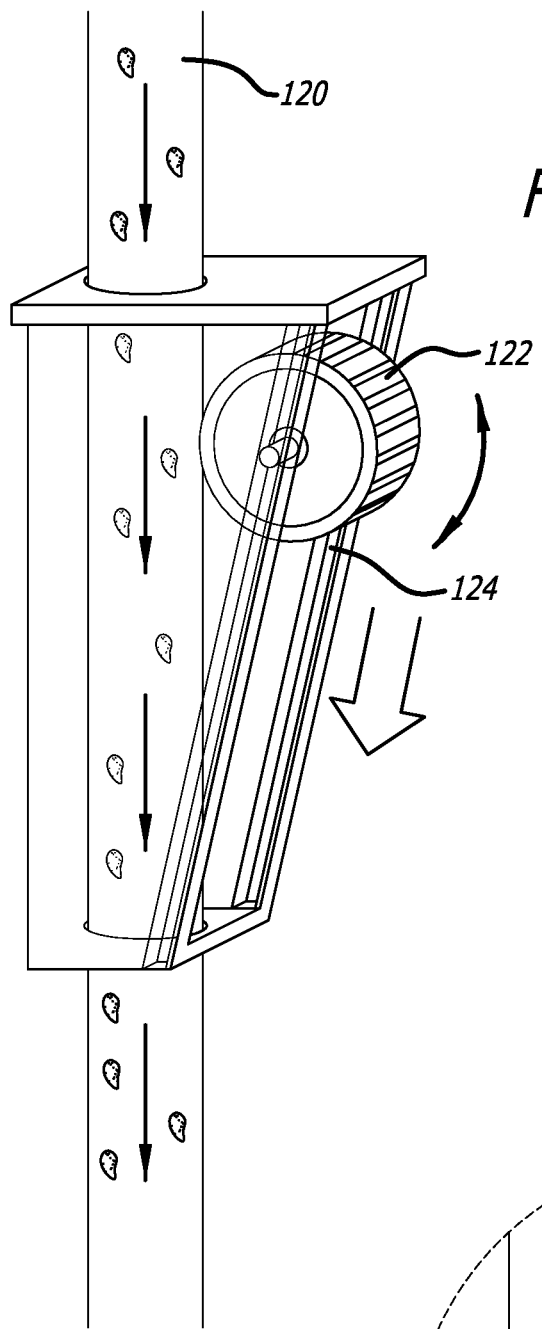
FIG. 9A illustrates a manual flow control mechanism of the present invention.
Figure 9B:
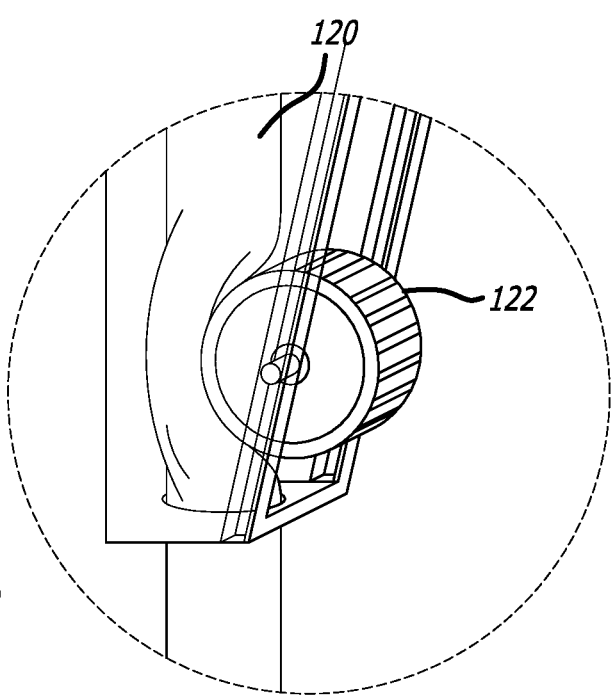
FIG. 9B shows the manual flow control mechanism of FIG. 9A is the closed position.

Removing the waste material can take several forms. When a siphoning action is used, the effluent flow rate may be controlled by a wheel type flow control system (FIGS. 9A, 9B). A wheel 122 is mounted on an inclined guide 124 proximal to the effluent syphon tube 120, where rotation of the wheel 122 such as by use of the thumb rolls the wheel 122 into contact with the tube 120. Further rotation pushes the wheel into engagement with the tube, collapsing the tube and constricting the flow of fluid and effluent in the tube (FIG. 9B). Fully rotating the wheel to the end of the rail substantially closes the tube 120, thereby providing complete control over the flow through the tube. Such a device, by its compression of the effluent tube 120, changes flow by a fourth power of the radius. Decreasing the radius by half decreases flow to one-sixteenth of the original value (Poiseuille's Law). Such a system allows for simple yet sensitive control of effluent flow, balancing waste removal against proper fluid inflation and cleansing of the colon.

Figure 10:
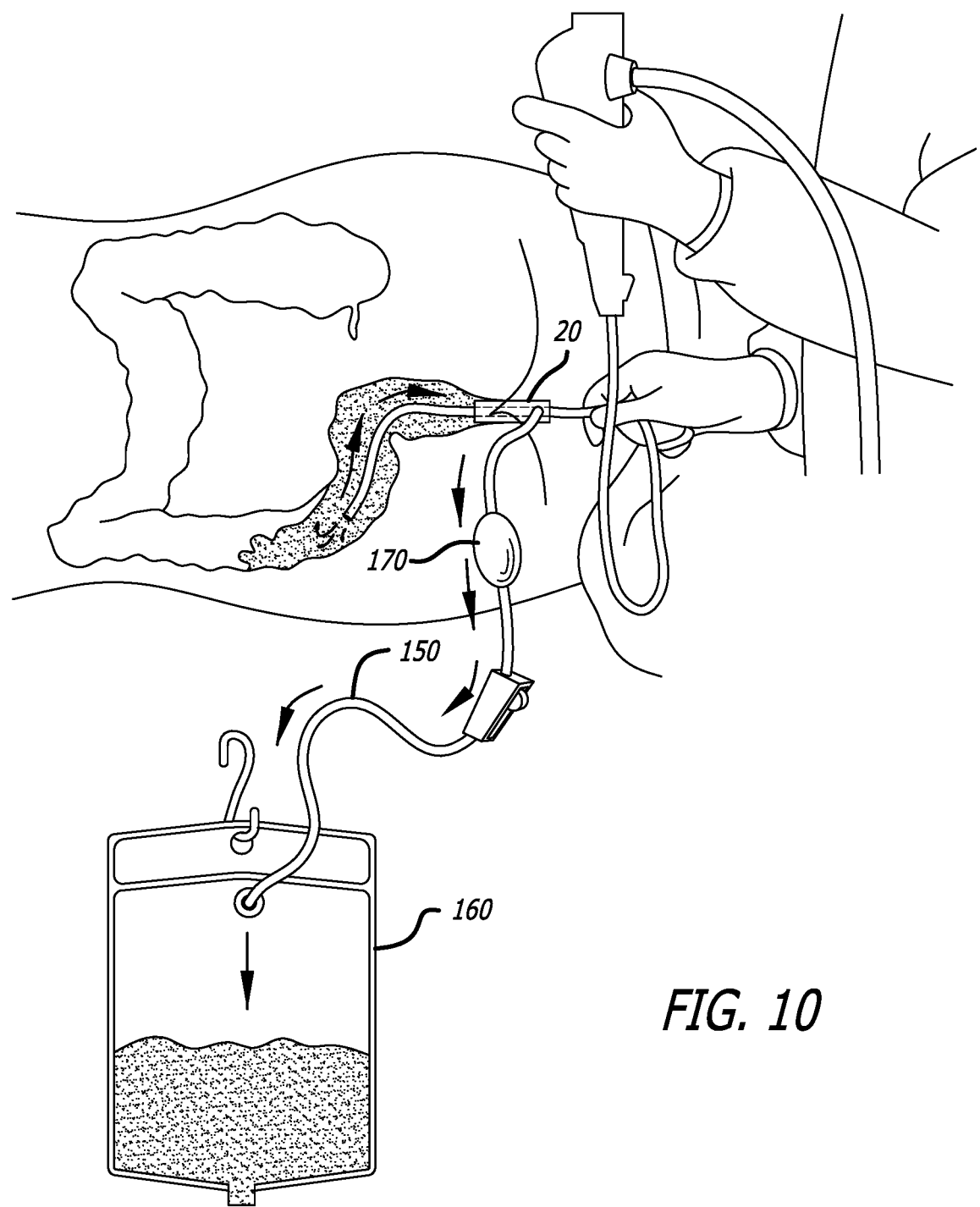
FIG. 10 is an illustration of the system of the present invention with a first draining system.

FIG. 10 illustrates an alternate flow control for the system of the present invention. This new lavage fluid and waste removal technique makes use of the intraabdominal and intracolonic pressure produced by the abdominal wall, viscera, colonic wall, and luminal water level in the closed system of the colon due to the presence of the sealed overtube 20. A drainage line 150 extends from the overtube 20 to a receptacle 160, either open or closed, on the floor or a position lower than that of the patient (siphonic physics-Bernoulli Equation). This produces a siphonic action using extraluminal and intraluminal (fluid) pressure and gravity aided by the sealed nature of the system to help initiate a constant outflow of fluid and waste. The more fluid, the more pressure, the more cleansing action, and better waste removal not to mention a cleaner procedure. Flow rate through the drainage tube is adjustable to balance water infusion and waste removal to maintain proper colonic luminal dilation for better observation and procedure performance as well as cleansing.

To assist in the establishment, maintenance and if necessary, reestablishment of siphonic action in the water/waste removal line, an integral squeeze-type balloon pump 170 may be used. This is useful to keep the line free from obstruction from blood, stool and other materials as well as maintain or reinitiate siphonic action. The balloon pump 170 includes two one-way valves, defaulted to an open position, that allows normal free fluid flow through the pump but close appropriately when necessary, to establish fluid and waste flow and remove obstruction in the line. This technique uses principals of physics to affect siphonic fluids/waste removal as previously mentioned in absence of a dedicated ancillary vacuum system. The system is easy to setup and use, is of a simple design using no moving parts. It places minimal demands on material needs and staff interventions.

Keeping the colonoscope in proper position and with the removal of the insertion port covering 50 by sliding it backward from the port 23 over the colonoscope insertion tube toward the colonoscope control handle opens a wider site egress for waste material (approximately 2.0 to 2.1 centimeters in diameter). Constant water infusion from the water jet distal end of the insertion tube produces an enema effect to flush out residual liquid and solid waste through the open insertion opening 23 that would be problematic for the smaller vacuum port 22 of the overtube 20. The insertion port covering 50 could be easily slid back into position over the colonoscope and resealed.

The cap 56 is used to close the central opening in the insertion port. This helps to retain water and prevent air from entering the colon should the colonoscopist wish to remove and then reinsert the colonoscope to continue the procedure.

Figure 11:
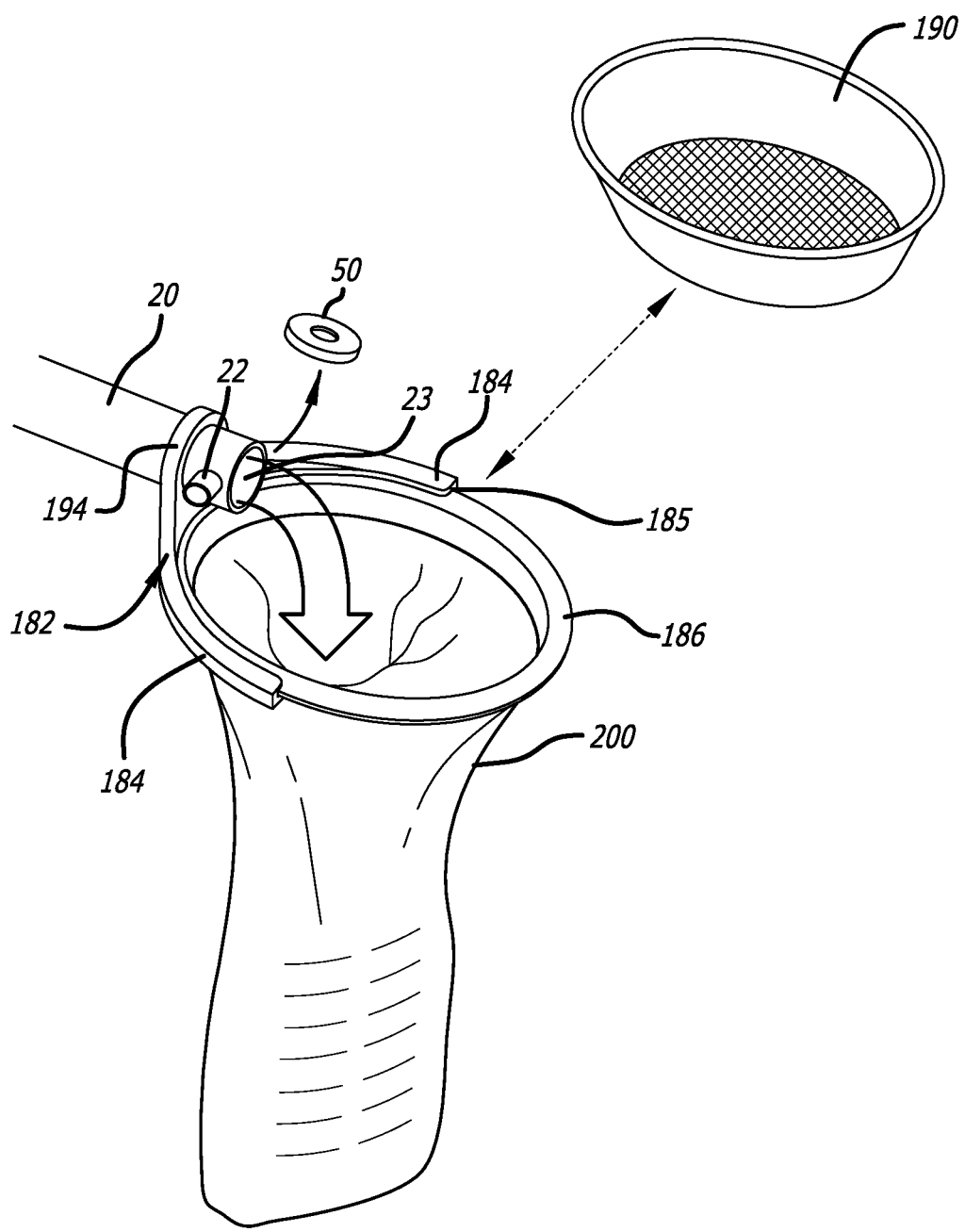
FIG. 11 is an illustration of the system of the present invention with a bracket assembly for connecting an emesis bag.

FIG. 11 further illustrates how the effluent flow can be directed out of the overtube through the opening 23. This mode makes use of a bracket attachment 182 on the overtube which holds an emesis bag 200 in proper position to collect waste effluent when the flexible covering over the colonoscope insertion port is removed. The bracket attachment 182 is mounted on the overtube adjacent to its proximal end to secure the emesis bag 200 below the opening 23 of the overtube 20. The bracket attachment 182 may include first and second arms 184 that form a semi-circular support with a channel 185 that receives a rim 186 of the emesis bag 200 therebetween. This is especially useful in maintaining the cleanliness of the endoscopy suite, endoscopy platform (table, gurney, or bed) and the patient during polyp removal, foreign body removal, removal of waste material too large or viscous to be cleared through the waste port or clearance of waste obstructing the entrance to the waste port from the overtube. A screen attachment 190 which is inserted into the opening of the emesis bag strains for polyps or other material which could not pass through the vacuum channel or were lost during the removal process. The bracket attachment 182 clamps onto the overtube 20 using a hinged clamp 194 that can quickly be released and disconnected from the overtube for removing or replacing the bag 200.

While this disclosure has described and depicted multiple embodiments of the present invention, it is to be understood that the invention is not limited to any single embodiment or depiction. Rather, the various features and elements of the disclosure are understood to be combinable where appropriate to create various combinations and arrangements of the various elements of the invention. Thus, nothing in this disclosure should be construed as limited to any particular embodiment shown or described.

I claim:

1. A system for performing a water cycling colonoscopy, comprising:
    a colonoscope having a camera and a fluid conduit;
    a fluidic vacuum source configured to withdraw fluid from a body cavity via a vacuum tube; and
    an overtube configured to receive the colonoscope at a proximal end and extend the colonoscope through a distal end, the overtube comprising:
        a vacuum port fluidly connected to an interior volume of the overtube, and configured to receive the vacuum tube thereon to connect the overtube's interior volume to the fluidic vacuum source;
        a frustoconical portion;
        a flexible skirt disposed between the vacuum port and the frustoconical portion, the flexible skirt abutting the frustoconical portion and having an outer diameter greater than an outer diameter of the frustoconical portion and configured to establish an airtight seal with an adjacent tissue and positioned to form an obtuse angle with the frustoconical portion; and
        a removeable closure covering enclosing a proximal end of the overtube, the removeable closure covering proximal to the vacuum port.

2. The system of claim 1, further comprising an adhesive coating on the flexible skirt on only a proximal facing surface.

3. The system of claim 2, wherein the closure covering includes a circular hole that allows for passage of the colonoscope while maintaining a seal around the colonoscope.

4. The system of claim 1, further comprising an introducer sized to pass through the overtube and adapted to expand tissue surrounding an anus for insertion of the overtube.

5. The system of claim 1, wherein the vacuum port is disposed on a portion of the overtube, said portion configured to rotate three hundred sixty degrees about a longitudinal axis with respect to a remaining portion of the overtube.

6. The system of claim 1, wherein a portion of the overtube adapted to be inserted into a patient is inflatable to an open position from a deflated, closed position while inside the patient.

7. The system of claim 1, further comprising a manual flow control valve configured to adjust a flow rate through the vacuum tube.

8. The system of claim 7, wherein the manual flow control valve comprises a thumb wheel.

9. The system of claim 1, further comprising a bracket mounted on the overtube adjacent the proximal end of the overtube, the bracket adapted to secure an emesis bag below a proximal opening of the overtube.

10. The system of claim 9, further comprising an emesis bag and a removable screen cooperating with the emesis bag to collect solid objects exiting the overtube through the proximal opening.

11. The system of claim 9, wherein the bracket includes first and second arms that form a semi-circular support with a channel.

12. The system of claim 1, wherein the fluidic vacuum source is connected to both the vacuum tube of the overtube and the colonoscope.

13. The system of claim 1, further comprising an inflatable cuff at the distal end of the overtube, said inflatable cuff expandable from a closed frustoconical shape to an open funnel shape.

14. The system of claim 1, further comprising a thumbwheel configured to adjust a syphon flow of effluent through the vacuum tube.

15. The system of claim 1, wherein the fluidic vacuum source is a manual pump that induces syphonic action to remove fluid from a patient.

* * * * *